US006633771B1

(12) United States Patent
Braig et al.

(10) Patent No.: US 6,633,771 B1
(45) Date of Patent: Oct. 14, 2003

(54) SOLID-STATE NON-INVASIVE THERMAL CYCLING SPECTROMETER

(75) Inventors: James R. Braig, Piedmont, CA (US); Bernhard B. Sterling, Danville, CA (US); Joan C. Godfrey, Fremont, CA (US); Julian M. Cortella, Alameda, CA (US); David J. Correia, Fremont, CA (US); Charles E. Kramer, Poway, CA (US); Arthur M. Shulenberger, Brisbane, CA (US)

(73) Assignee: OptiScan Biomedical Corporation, Alameda, CA (US)

( * ) Notice: Subject to any disclaimer, the term of this patent is extended or adjusted under 35 U.S.C. 154(b) by 0 days.

(21) Appl. No.: 09/427,178

(22) Filed: Oct. 25, 1999

Related U.S. Application Data

(63) Continuation-in-part of application No. 09/265,195, filed on Mar. 10, 1999, now Pat. No. 6,198,949.

(51) Int. Cl.[7] ............................ A61B 5/00; G01N 21/71

(52) U.S. Cl. ................ 600/310; 250/339.03; 250/341.6

(58) Field of Search ................................ 600/310, 316, 600/322, 473; 250/341.1, 341.6, 341.5, 341.8, 339.07, 339.03, 339.06, 339.12, 339.11, 339.09, 340, 455.1; 219/553; 392/407, 416, 483

(56) References Cited

U.S. PATENT DOCUMENTS

| | | | | | |
|---|---|---|---|---|---|
| 5,191,215 | A | * | 3/1993 | McClelland et al. | 250/341.6 |
| 5,291,022 | A | | 3/1994 | Drake et al. | 250/504 |
| 6,002,953 | A | | 12/1999 | Block | 600/316 |
| 6,072,180 | A | * | 6/2000 | Kramer et al. | 250/341.6 |

* cited by examiner

*Primary Examiner*—Eric F. Winakur
(74) *Attorney, Agent, or Firm*—Knobbe, Martens, Olson & Bear, LLP

(57) ABSTRACT

A solid-state device for the non-invasive generation and capture of thermal gradient spectra from sample tissue. The device includes an infrared transmissive layered window assembly, a means for inducing a thermal gradient in sample tissues. Also provided is an infrared radiation detector for detecting infrared emissions emanating from the tissue as the transient temperature gradient progresses into the sample tissues. The sensor provides output signals proportional to the detected infrared emissions. A data capture means is provided for the sampling of output signals received from the infrared radiation detector as the induced temperature gradient progresses into the sample tissue.

68 Claims, 6 Drawing Sheets

SOLID-STATE NON-INVASIVE THERMAL CYCLING SPECTROMETER

RELATED APPLICATION

This application claims priority to and is a continuation-in-part of the application filed on Mar. 10, 1999, entitled "Solid-State Non-Invasive Infrared Absorption Spectrometer for the Generation and Capture of Thermal Gradient Spectra from Living Tissue", identified by U.S. Pat. Ser. No. 09/265,195, now U.S. Pat. No. 6,198,949.

TECHNICAL FIELD

The present invention relates to an apparatus for inducing transient thermal gradients in human or animal tissue, and for obtaining infrared spectra from the tissue as the thermal gradient propagates through the tissue. The resulting infrared spectra may then be used to determine concentration of substances (analytes) present in the tissue, for example, glucose.

BACKGROUND OF THE INVENTION

Millions of diabetics draw blood daily to determine blood glucose levels. Substantial effort has been expended in a search for a non-invasive method of accurately determining blood glucose concentrations. To that end, Optiscan Biomedical Corporation of Alameda, Calif., has significantly advanced the state of the art of non-invasive blood glucose analysis. In a series of patents and patent applications, Optiscan has defined the state of the art for non-invasive blood glucose determination.

The methodologies taught in U.S. patent application Ser. Nos. 08/820,378 and 09/267,121 may be performed by the apparatuses taught in U.S. patent application Ser. Nos. 08/816,723 and 09/265,195, and each of these references is hereby incorporated by reference.

By way of introduction, objects at temperatures greater than −273.16° C. (absolute zero) emit infrared energy. Such emissions are often described by Planck's Equation and referred to as "black body curves". Theoretically, a body having an emissivity of 1.0 shows perfect agreement with Planck's Equation. Advantageously, many objects have emissivity close to 1.0. In particular, human tissue has emissivity of approximately 0.9 to 0.98. It is well known that infrared emissions from the human body may be closely approximated by Planck's Equation and yield black body type emission spectra.

Although the human body emits energy having a distribution that approximates that described by Planck's Equation, Planck's Equation does not completely describe the sum total of all energy emitted by a human body. Variations from perfect agreement with Planck's Equation are caused by selective absorption of radiation by the layers of tissue and body fluid in the human body. Thus, layers of tissue and blood or other fluids may selectively absorb emitted energy from the deeper layers of the body before that energy can reach the surface of the skin. Furthermore, because the deeper layers of the human body are warmer than the outer layers, a temperature gradient exists within the body. This causes a further deviation from theoretical black body radiation emission.

However, the inventors have determined that, when the above two conditions exist, a composition-dependent absorption spectra may be constructed from proper analysis of the total energy emitted from the body. For heterogeneous bodies, the composition of matter may be depth dependent and, conversely, absorption spectra generated from deeper layers may contain sufficient composition information to allow accurate determinations of concentration of the individual constituents present in the tissue. This is possible when a temperature gradient either occurs naturally, or is induced in the body.

The invention taught in U.S. patent application Ser. No. 08/820,378 ('378) uses the naturally occurring body temperature as the source of infrared emissions. As these infrared emissions, which have emanated from deeper inside the body, pass through layers of tissue that are closer to the surface, certain wavelengths of energy are selectively absorbed by the intervening tissue. This selective absorption of signal produces bands of reduced energy in the expected emission spectra when the energy finally exits the material under study. This spectra is referred to as the absorption spectra of the material.

The invention taught in U.S. patent application Ser. No. 08/816,723 ('723) uses actively induced cooling to promote the selective absorption of radiation by causing a temperature gradient to propagate to selected layers of tissue, which typically range between 40 and 250 $\mu$ below the tissue surface. As explained in the '723 application, absorption spectra of the tissue may be measured and the determination of glucose concentration may be made.

An additional technique for determining the concentration of substances ("analytes") in a tissue sample is set forth in U.S. patent application Ser. No. 09/267,121 ('121). The '121 application describes a method of measuring infrared emissions emitted by a tissue sample subject to a temperature gradient. By detecting emitted signals at selected wavelengths and comparing them to carefully selected reference signals, a frequency or a magnitude or a phase difference between the reference signal and an analytical signal may be used to determine analyte concentration. Furthermore, the method taught in the '121 application teaches the use of an intermittently or periodically modulated temperature gradient and the continuing measurement of frequency, magnitude, or phase differences caused by analyte absorbance to determine analyte concentration. Furthermore, the '121 application teaches a method of correcting for the effects caused by tissue surfaces.

According to U.S. patent application Ser. No. 08/820,378 ('378), there is provided a spectrometer for the non-invasive generation and capture of thermal gradient spectra from human or animal tissue. The '378 spectrometer includes an infrared transmissive thermal mass for inducing a transient temperature gradient in the tissue by means of conductive heat transfer with the tissue, and a cooling means in operative combination with the thermal mass for cooling this thermal mass. There is also provided an infrared sensor for detecting infrared emissions emanating from the observed tissue as the gradient progresses into the tissue. Also included is a data capture means for sampling the output signals received from the sensor as the gradient progresses into the tissue. The '723 invention uses a cooled germanium cylinder brought into intermittent contact with the test subject's tissue. The resulting gradients are used to perform the methodology taught in Application '378. Skin rewarming, according to this invention, is accomplished by simply allowing the patient's skin to naturally rewarm after each cooling contact. Alternatively, rewarming may be accomplished by an external heat source in the form of a second warmer germanium cylinder. U.S. patent application Ser. No. 09/265,195 ('195) provides a "solid-state" apparatus for creating and measuring the effects of transient thermal gradients on tissue. The '195 application teaches a single thermal mass structure ("a thermal mass window") which both heats and cools the tissue and is capable of transmitting the absorption spectra generated by the gradient. This allows the window to remain in contact with the tissue during the entire time measurements are made, thereby improving accuracy and measurement repeatability.

The inventors discovered that by inducing a cyclic temperature gradient certain measurement advantages accrue. These advantages are more apparent when a fairly rapid cooling/rewarming cycle time (hereinafter referred to as "cycle time") is used. Cycle times on the order of 2 Hz are preferred. Existing devices encountered some difficulties obtaining the requisite cycle times due to residual heat or cooling remaining in the thermal mass structures after heating and cooling steps. Thus, it took excessive time and energy to cyclically induce the cooling and heating steps. There is a need for a thermal gradient device that can induce temperature gradients more quickly and using less energy. An advantage of devices which generate gradients using less energy is that smaller devices may be constructed.

SUMMARY OF THE INVENTION

According to the principles of the present invention there is provided a solid-state device for determining analyte concentrations within sample tissues. The device generates a thermal gradient in the tissue and measures infrared radiation spectra to make determinations of tissue analyte concentration. The device comprises an infrared transmissive window assembly having a plurality of infrared transmissive elements, one of which being a heating element, another being an insulating element. The device also has a cooling element in operative combination with the insulating element. The device also comprises an infrared detector for detecting an infrared radiation spectrum as it passes through said window assembly.

An important aspect of the invention is a thermal insulating and impedance matching element positioned between the heating and cooling elements. Yet another embodiment of the invention enhances the ability of the device to rapidly cycle through the cooling/rewarming cycle by including a heat sink in thermal contact with the cooling element. This effectively stabilizes the temperature in the device during cycling. This heat stability is enhanced through the use of a phase change material.

Other features of the invention are disclosed or apparent in the section entitled "DETAILED DESCRIPTION OF THE INVENTION".

BRIEF DESCRIPTION OF THE DRAWINGS

For a more comprehensive understanding of the present invention, reference is made to the accompanying drawings in the following Detailed Description of the Invention. In the drawings.

Reference numbers refer to the same or equivalent parts of the invention throughout the several figures of the drawings.

DETAILED DESCRIPTION OF THE INVENTION

The present invention relates to the measurement of infrared (IR) radiation emitted by heterogenous bodies. In particular, an apparatus for inducing a temperature gradient in a tissue sample and measuring the IR radiation spectra emitted from the tissue. The following description is presented to enable one of ordinary skill in the art to make and use the invention as provided in the context of a particular application and its requirements. Various modifications to the preferred embodiments will be readily apparent to those skilled in the art, and the generic principles defined herein may be applied to other embodiments. The present invention is not intended to be limited to the embodiments shown, but is to be accorded the widest scope consistent with the principles and novel features disclosed herein.

A discussion of the principles of non-invasive infrared spectrometry applied to analyte quantification can be found in the incorporated references.

The present invention teaches a method and apparatus for creating and controlling the magnitude, propagation, velocity, and contour profile of a thermal gradient, and incorporates cyclic cooling and rewarming of a sample observation site. Furthermore, the present invention teaches the detection and measurement of infrared spectral emissions from the sample tissues.

Figure 1:
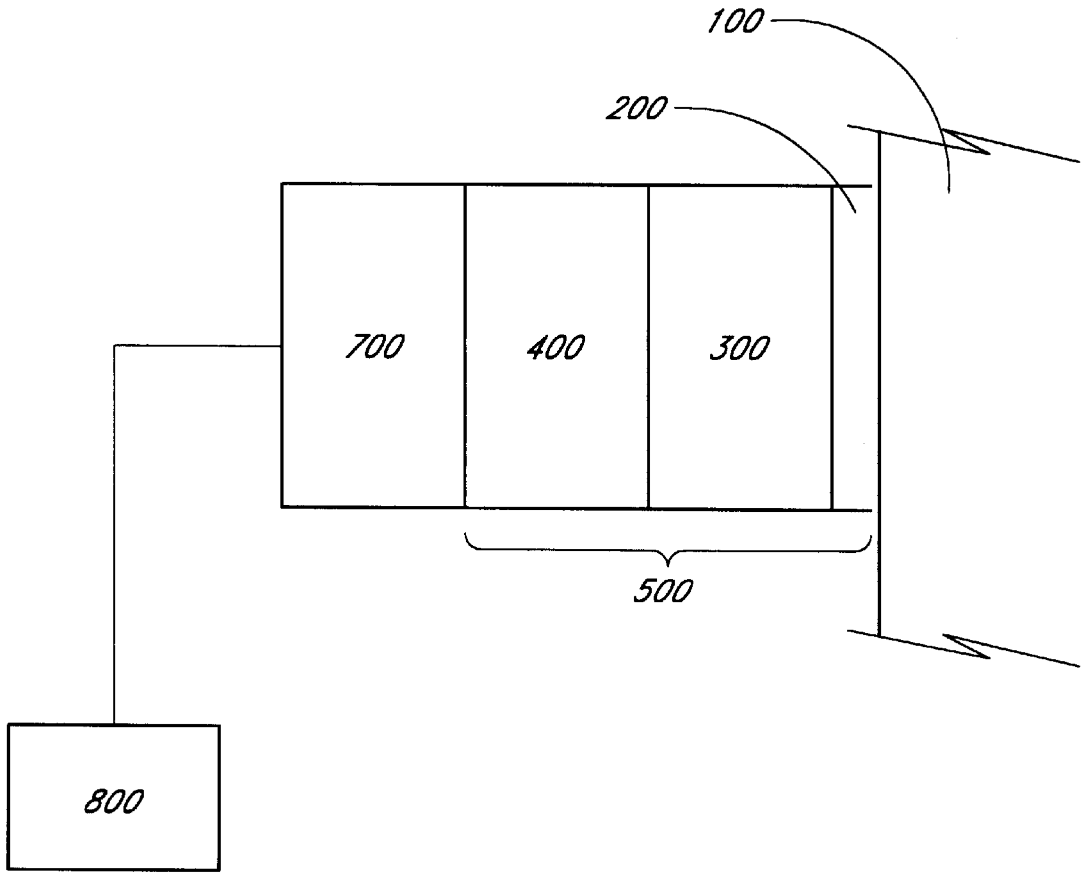
FIG. 1 is a schematic depiction of an apparatus constructed in accordance with the principles of the present invention.

Referring to FIG. 1, a block diagram of an embodiment of the present invention is shown. The embodiment shown provides a solid-state thermal gradient inducing device 500 for inducing a temperature gradient within a tissue sample 100. The infrared emissions from the body are then transmitted through the thermal gradient device 500 where they are collected by an infrared radiation detector assembly 700. The detector assembly 700 receives the infrared emissions from the tissue 100 and measures certain wavelength information which is passed on to a signal processing system 800 which processes the information. The several elements of the system will be described below.

The solid-state thermal gradient device 500 is comprised of three general components: An infrared transmissive window assembly 200 which provides direct contact with a tissue sample 100 permitting the transmission of infrared radiation from the tissue sample to the IR radiation detector assembly 700. The solid-state thermal gradient device 500 also includes a means 300 for inducing a temperature gradient in the tissue sample 100. This means 300 typically includes a heating element and a cooling element. The heating element may be integral to the infrared transmissive window assembly 200. Finally, the solid-state thermal gradient device 500 incorporates a heat sink 400 which is in thermal communication with the cooling element.

Window Assembly 200

Figure 2:
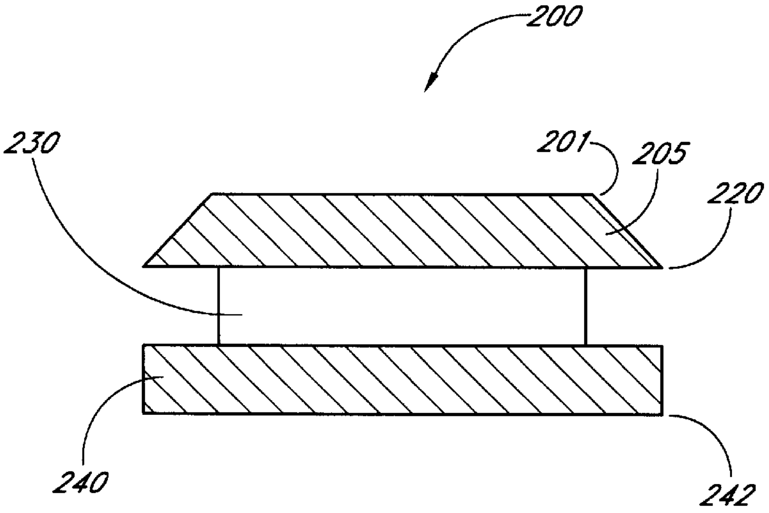
FIG. 2 is a cross-sectional view of a layered window assembly of the present invention.

In one preferred embodiment of the present invention, as shown in FIG. 2, the solid-state thermal gradient device 500 includes an infrared transmissive window assembly 200. The window assembly 200 includes a plurality of infrared transmissive elements which may be constructed in a layered fashion.

Figure 3:
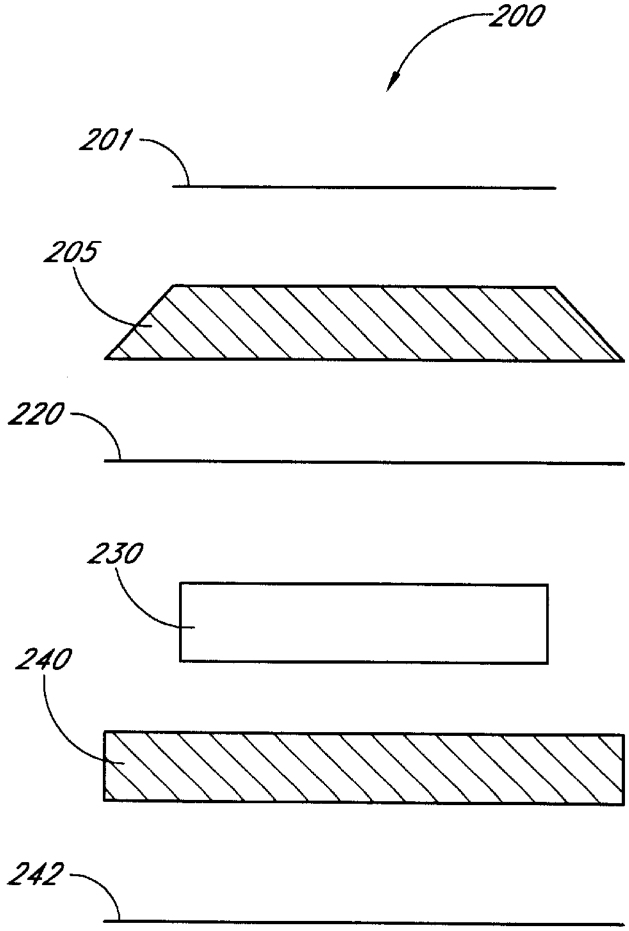
FIG. 3 is an exploded cross-sectional view of the layered window assembly of FIG. 2.

FIG. 3 depicts a layered window assembly 200. The window assembly features an infrared transmissive thermally conductive spreader layer 205. Underlying the spreader layer 205 is a heater or heating element 220. This heating element 220 can be treated with a thin electrically insulating layer (not shown). Adjacent to the heating element 220 is a thermal insulating and impedance matching element 230. Adjacent to the thermal insulating element 230 is a thermally conductive base layer 240. The thermally conductive spreader layer 205 is coated on its top surface with a thin layer of protective coating 201. The bottom surface of the base layer is coated with a thin overcoat layer 242. Preferably, protective coating 201 and overcoat layer 242 have antireflective properties.

The spreader layer 205 is preferably formed of infrared transmissive material having a high thermal conductivity sufficient to facilitate heat transfer from the heater element 220 uniformly into the tissue sample 100. A satisfactory material is silicon crystal formed using a float zone crystal growth method. A generalized discussion of this method of silicon fabrication may be found in *Microchip Fabrication, A Practical Guide to Semiconductor Processing*, 3*rd Ed*., Peter Van Zant, McGraw Hill 1997, which is hereby incorporated by reference. Other effective materials include, but are not limited to, chemical vapor deposited diamond, diamondlike carbon, gallium arsenide, germanium, and other IR transmissive materials having sufficiently high thermal conductivity. Preferred dimensions for the spreader layer 205 are about one inch in diameter and about 0.010 of an inch thick. FIG. 3 shows a preferred embodiment of the spreader layer 205 with a beveled edge. Although not required, an approximate 45° bevel is preferred.

A protective layer 201 is formed on the top surface of the spreader layer 205. The protective layer is intended to protect the top surface of the spreader layer 205 from damage. Ideally, the protective layer is highly resistant to mechanical damage, such as scratching and other abrasive forces. Additionally, the protective layer is infrared transmissive. It is particularly advantageous if the protective layer 201 is also optimized to have antireflective properties and to increase transmission of optical radiation in the wavelength range of about 5 to 12 $\mu$. For example, when a float zone silicon is used as a spreader layer 205, the spreader layer reflects 30% of the incident light at the air:silicon interface because of the relatively high refractive index of silicon. The protective layer 201 is designed to match the refractive index of tissue and reduce the surface reflectance of the spreader layer 205, thereby optimizing the amount of energy passing through the window assembly 200. The protective layer 201 must also have high thermal conductivity. A satisfactory protective layer material is a proprietary multi-layer Broad Band Anti-Reflective Coating produced by Deposition Research Laboratories, Inc. of St. Charles, Mo. Diamondlike carbon coatings are also satisfactory.

Underlying the spreader layer 205 is a heating element 220. The heating element 220 must also provide a maximum acceptable optical throughput and should be electrically insulated from the spreader layer substrate material. A preferred heating element 220 obscures about 10% or less of the window assembly 200. Satisfactory heating elements include, but are not limited to, heat exchangers, electrical resistance heating grids, thermal electric heaters, radio frequency (RF) heaters, infrared radiation heaters, optical heaters, or wire bridge heating grids. Additionally, a doped infrared transmissive material with regions of higher and lower resistivity may be used. For example, a doped silicon layer may be used as a heater.

Figure 4B:
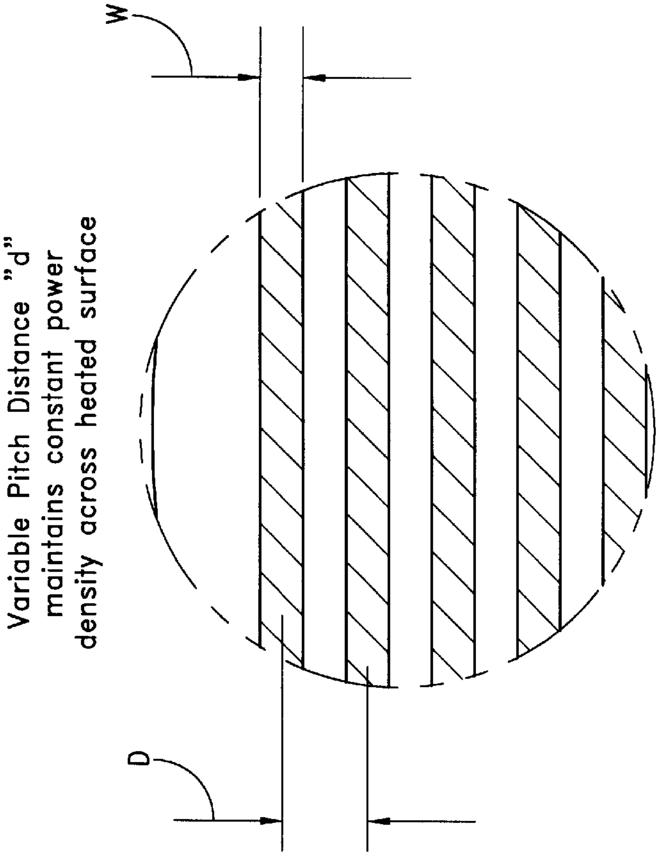
FIG. 4B is an exploded view of the heater grid of FIG. 4A taken along section 4B–4B.
Figure 4A:
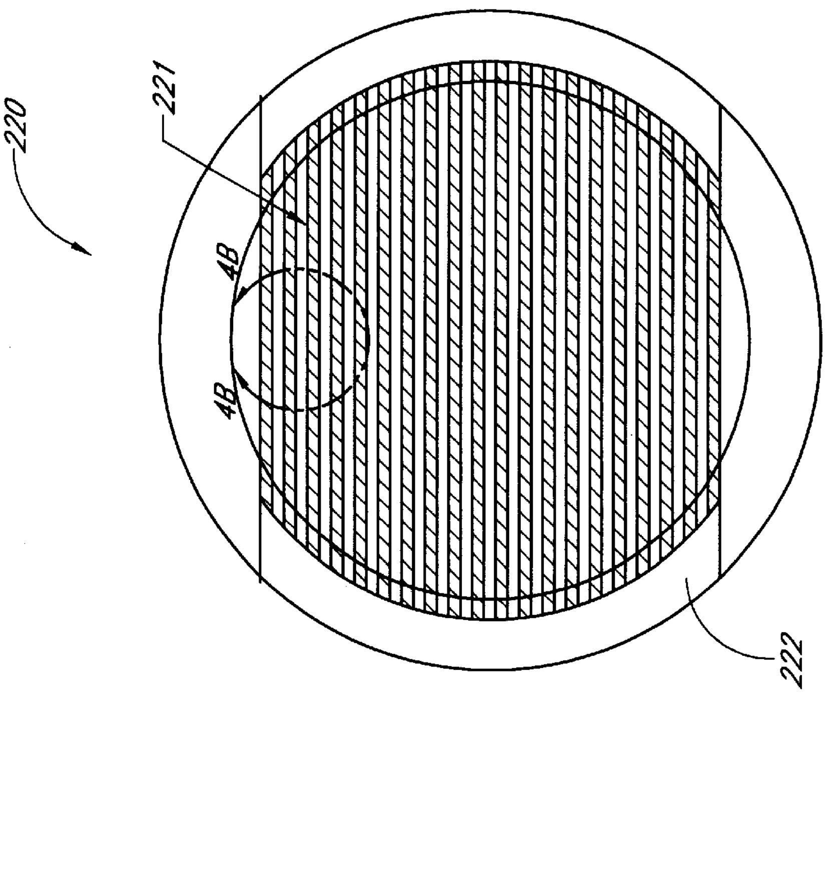
FIG. 4A is a plan view of a heater grid of the present invention.

One embodiment of such a heater element 220 is the heating grid shown in FIGS. 4A and 4B. The embodiment shown in FIGS. 4A and 4B shows a metal heater grid 221 designed and manufactured by Deposition Research Laboratories, Inc. The heater grid 221 has a resistance of about 2 ohms and has a preferred thickness of 1,500 Å. A preferred grid material is a gold alloy, but other acceptable materials include, but are not limited to, platinum (Pt), titanium (Ti), tungsten (W), copper (Cu), and nickel (Ni). The perimeter of the grid is surrounded by a bus bar 222 for contacting electrode leads. The heater 220 is covered with an electrically insulating coating which also enhances adhesion to the spreader layer 205. One preferred covering is an aluminum oxide ($Al_2O_3$) coating over the grid pattern to prevent electrical current from conducting through the spreader layer 205 into the tissue 100. $Al_2O_3$ also advantageously increases the adhesion of the heater element 220 to the spreader layer 205. Other acceptable materials include, but are not limited to, titanium dioxide ($TiO_2$) or zinc selenide (ZnSe). The heater grid 221 is electrically connected to an electrical power source through the bus 222. A preferred bus bar material is gold. One preferred example of a heater grid incorporates a variable pitch distance "d" between the conducting lines to maintain a constant power density across the entire grid 221. In this embodiment a preferred line width "w" is about 25 microns. Another design for maintaining a constant power density across the entire grid 221 incorporates varying line widths "w" while keeping the pitch distance "d" constant.

Referring again to FIGS. 2 and 3, underlying the heater 220 is a thermal insulating layer 230. The thermal insulating layer 230 serves several novel and surprising functions which will be discussed in more detail below. The thermal insulating layer 230 prevents the dissipation of heat from the heater element 220 while allowing the cold from a cooling element (not shown) to effectively cool the tissue 100. The thermal insulating layer 230 is comprised of a material having thermally insulative (e.g., lower thermal conductivity than the spreader layer) and infrared transmissive qualities. A preferred material is a germanium arsenic selenium compound of the calcogenide glass family known as AMTIR-1 produced by Amorphous Materials, Inc. of Garland, Tex. A further description of this material may be found on that firm's material data safety sheet (MSDS). The pictured embodiment has a diameter of about 0.85 of an inch and a preferred thickness in the range of about 0.005 to about 0.010 of an inch. As the heating element 220 heats through the spreader layer 205 into the tissue 100, the thermal insulating layer 230 (having a low thermal conductivity) insulates this heat. Underlying the thermal insulating layer 230 is a base layer 240 which is formed of thermally conducting material. A preferred material is crystalline silicon formed using float zone crystal growth. The purpose of this base layer 240 is to serve as a cold-conducting mechanical base for the entire layered window assembly. The bottom surface of the base layer is treated with an overcoat layer 242. The overcoat layer 242 is preferably a proprietary multi-layer Broad Band Anti-Reflective Coating optimized for the transmission of radiation in the wavelength range between about 5 to about 12 $\mu$ and having the refractive index of air. Such coating materials are available from Deposition Research Laboratories, Inc. in St. Charles, Mo.

The overall optical transmission of the layered window assembly 200 is equal to or greater than 70%. The layered window assembly 200 is held together and secured to the gradient device 500 by a holding bracket. The bracket is preferably formed of a glass-filled plastic, for example, Ultem 2300, manufactured by General Electric. The Ultem 2300 has a low thermal conductivity which insulates the heat transfer from the layered window assembly 200. As such, the tissue 100 is solely heated and cooled by the heat and cold emanating from the layered window assembly 200.

Figure 5:
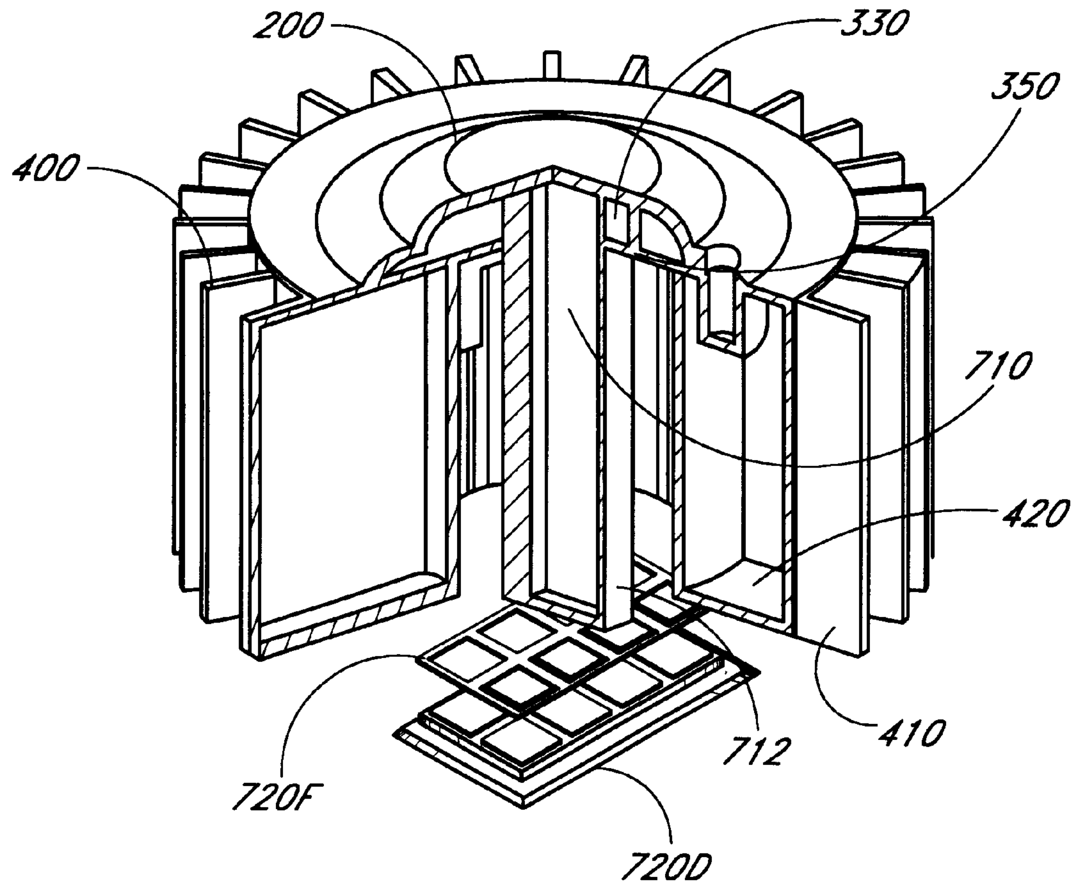
FIG. 5 is a cut-away perspective view of an apparatus illustrating the principles of the present invention.

Referring to FIG. 5, a portion of the entire solid-state non-invasive device for determining analyte concentration in sample tissues is shown. The layered window assembly 200 is depicted as resting above a cold reservoir 330 which is adjacent to the cooling element 350. The cooling element 350 may be selected from such elements as air cooled convection coolers, passive conduction coolers, such as heat sinks, or active conduction coolers, such as, thermal electric coolers. The cooling element 350 may be also selected from the group of cooling elements including, but not limited to, water baths, gas coolers using cold $N_2$ or other gases, or infrared transmissive cooling fluids. The preferred cooling element is a thermal electric cooler, for example, a 25 W thermal electric cooler manufactured by Melcor in Trenton, N.J. The cooling element 350 (hereinafter referred to as "thermal electric cooler" or "TEC") is positioned in thermal contact with the cold reservoir 330. A preferred cold reservoir 330 is a copper ring structure which is in thermal contact with both the layered window assembly 220 and the TEC 350.

It is the combination of the heating element 220, the thermal insulating element 230, the cold reservoir 330, and the cooling element 350 that comprises a means for inducing a temperature gradient in the tissue 100. Typically, this is accomplished by setting the cooling element 350 to a constant temperature of in the range of about 8–15° C. The heating element 220 is then cyclically activated to heat to a maximum of about 40° C. Thermal cycling the heating element 220 cyclically heats the layered window assembly 200 and induces a temperature gradient in the tissue 100.

Figure 6:
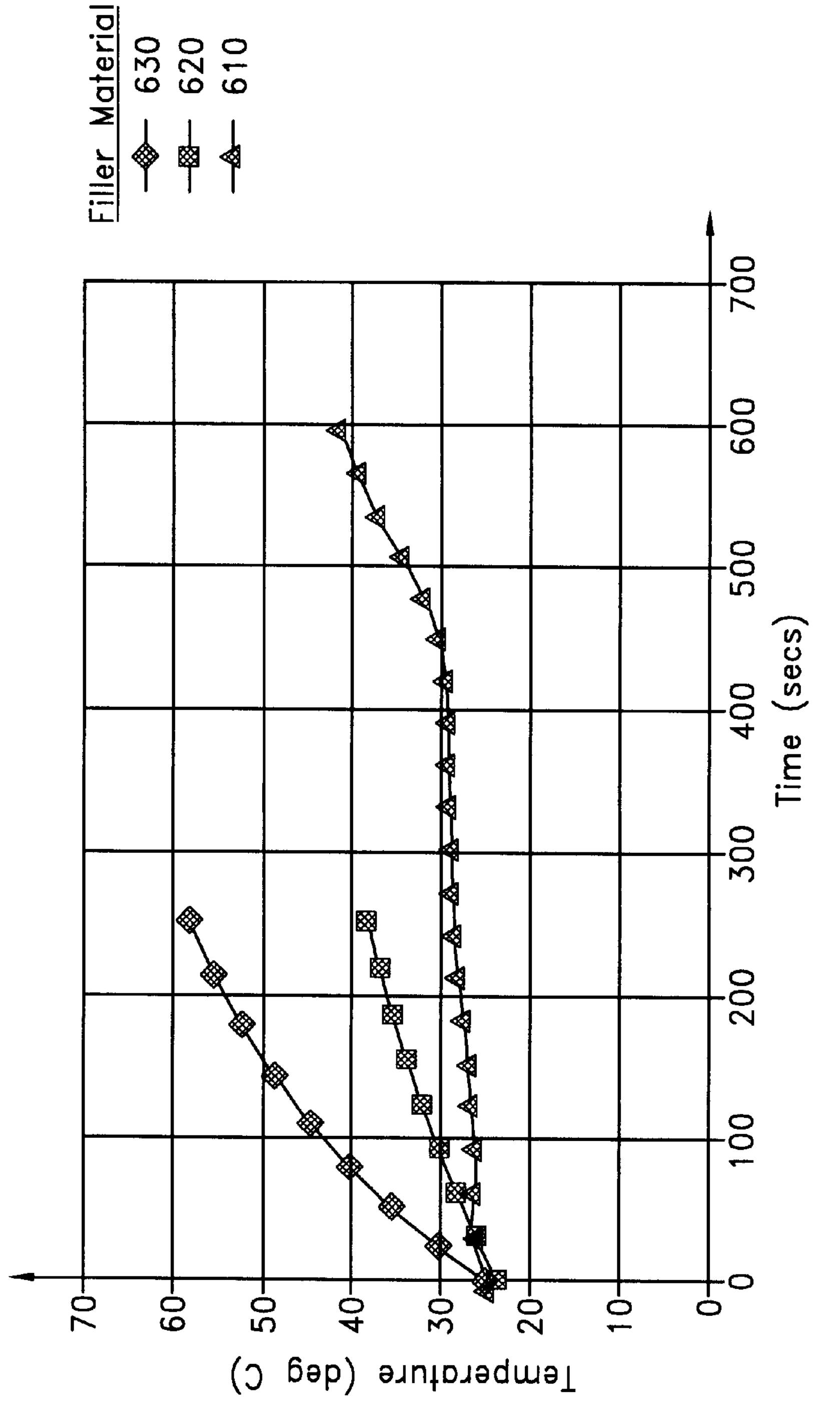
FIG. 6 is a graph of a temperature stability curve.

With continuing reference to FIG. 5, the inventors discovered that when a thermal electric cooler is chosen as the cooling element 350, a certain amount of waste heat builds up in the gradient device 500. In order to stabilize the operational temperature of the device, a heat sink 400 is in thermal communication with the TEC 350. The heat sink 400 effectively bleeds off the waste heat from the TEC 350, enabling the device 500 to function within a constant temperature range. Furthermore, the heat sink may have cooling fins 410 to enhance the cooling effectiveness of the heat sink 400. Additionally, the heat sink 400 features a cavity 420. The cavity may be filled with a phase change material 430 (not shown) to enhance the temperature stabilizing effect of the heat sink 400. A phase change material 430 as defined herein is any material which undergoes a temperature dependent change of phase. For example, water undergoes a phase change from ice to water. In the process of undergoing the phase change, such materials absorb a great deal of heat, thereby enhancing the effectiveness of the heat sink 400. A preferred phase change material 430 is a hydrated salt, such as calcium chloride hexahydrate. A proprietary version of this material, TH29, is produced by Phase Change Solutions, of Naperville, Ill. Further description of this material is included in that firm's MSDS which is incorporated by reference. This material has a melting point of 29° C., which is close to the working temperature of the device. The effectiveness of this phase change material 430 is clearly demonstrated in FIG. 6, which is a graph of temperature stability over time with the instrument operating normally. The temperature stability, over time, of a heat sink using TH29 610 has superior temperature stability performance than both water 620 and a heat sink 400 with no phase change material 630.

The ability of the gradient inducing means is further enhanced by the presence of the thermal insulating layer 230 of the layered window assembly 200. The thermal insulating layer 230 is positioned between the heating element 220 and the base 240. It was discovered by the inventors that, in the absence of the insulating element 230, the cold from the cooling element 350 excessively reduced the temperature of the heating element 220. This led to difficulties in reheating. In order to sufficiently rewarm the heating element 220 after such cooling, a great deal of power was required. Furthermore, the time required to heat the cooling element 350 to operational temperature prohibitively restricted the cycle time. Therefore, in an effort to increase the rate of heating and cooling and increase cycle time, a thermally insulating element 230 was added. The presence of the insulating element 230 helps the heating element 220 to maintain a consistent and relatively high temperature, thereby making it possible to reheat the heating element 220 and spreader layer 205 and, consequently, the tissue 100 more quickly. Of equal importance the insulating element makes reheating possible using less power. These factors make quicker cycle times possible. The surprising result is that the presence of the insulating layer 230 does not significantly inhibit the cooling effects of the TEC 350. Therefore, the gradient inducing means (i.e. the heating element 220, the thermally insulating element 230, and the cooling element 350) are substantially enhanced in their effectiveness by the presence of the thermally insulating layer 230.

The layered window assembly 200 is designed with the idea of transmitting the maximum amount of optical energy through the window 200. Furthermore, the cold reservoir 330, the thermal cooling element 350, and heat sink 400 are all designed to minimally obstruct the transmission of optical radiation. Positioned beneath the layered window assembly 200 is an infrared radiation detector assembly 700.

Figure 7:
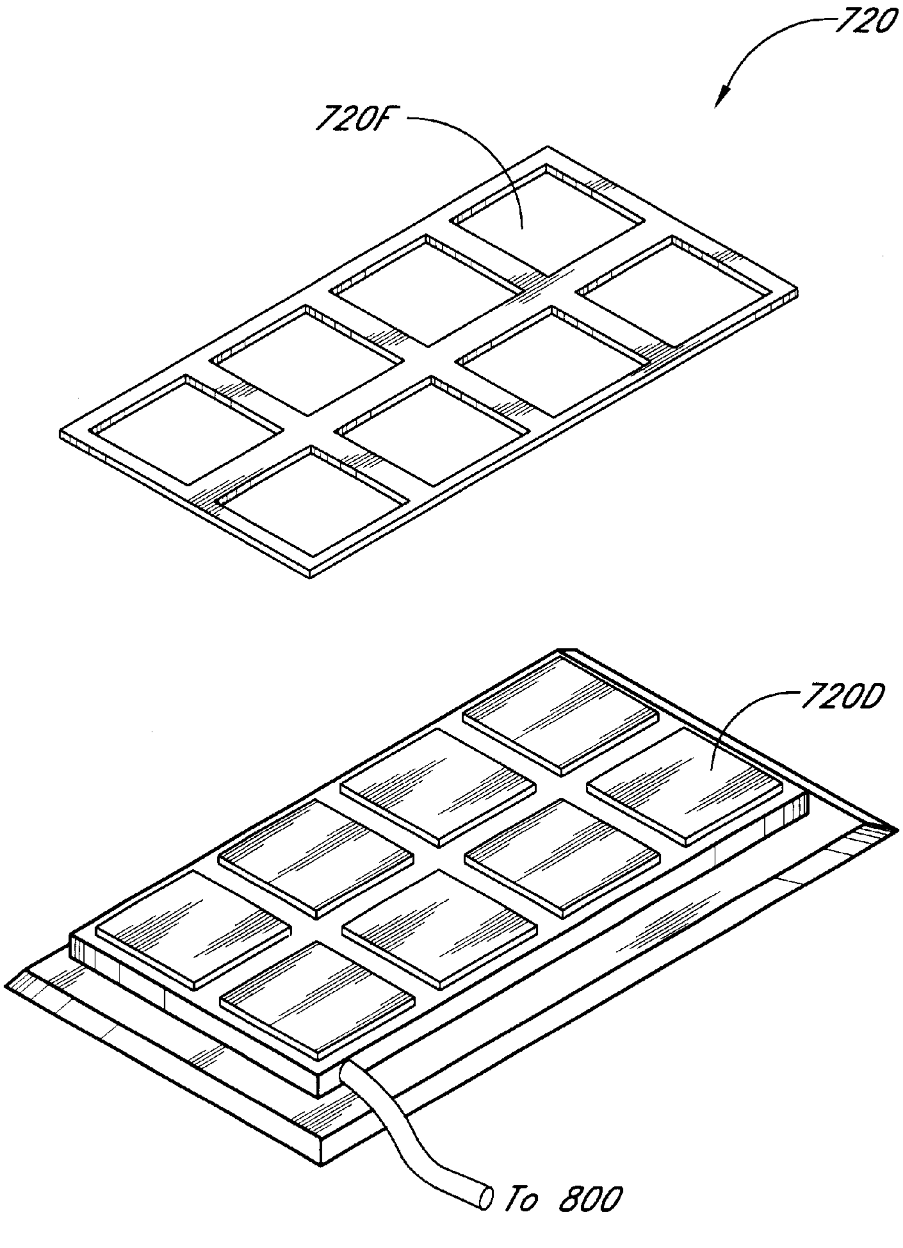
FIG. 7 is an exploded perspective view of a detector element of the present invention.

With reference to FIGS. 5 and 7, a particular embodiment of the infrared radiation detector 720, which forms a part of the infrared radiation detector assembly 700, is shown. It should be pointed out that many different types of radiation detectors may be utilized including, but not limited to, interferometers, spectrophotometers, grating monochromators, variable filter monochromators, and groups of discrete infrared bandpass filters (or Fabry-Perot filters, including tunable Fabry-Perot filters) and detectors. The effectiveness of said infrared radiation detector assembly 700 may be enhanced by the presence of a high reflectance scrambler 710. The scrambler 710 is designed to randomize the directionality of radiation which enters the layered window assembly 200. The scrambler 710 effectively minimizes the effect of tissue irregularities thereby maximizing the detectable signal. The scrambler 710 is either made from, or coated with, a material which does not preferentially absorb optical radiation in the range of about 5 $\mu$ to about 12 $\mu$. A satisfactory scrambler 710 may be constructed having an electroform gold layer. A satisfactory high reflectivity gold electroform optical scrambler 710 is manufactured by Epner Technology, of Brooklyn, N.Y. At the exit of the scrambler 712 lies a detector element 720. As explained above, the detector element 720 may be selected from among many suitable devices. One preferred embodiment uses a series of bandpass filters 720F having an underlying series of radiation detectors 720D.

One embodiment uses several bandpass wavelengths optimized to detect the presence of a glucose analyte in a tissue sample. Glucose has several strong and distinguishing absorption peaks between 9 and 10 microns; meaning the transmission of optical energy through glucose drops significantly in this wavelength range. As the infrared energy naturally emitted by the inner tissue passes through the glucose in the outer layers of the tissue, some of the energy in the 9.3 micron and 9.6 micron bands is absorbed.

At these particular wavelengths where glucose absorbs strongly, more energy originating deep within the tissue is absorbed before it reaches the surface. At other wavelengths where glucose is only weakly absorbent, a larger amount of energy from deep within the tissue finds its way to the surface. Additionally, at wavelength ranges where glucose doesn't absorb, for example about 8–9 microns, a reference signal which may be used for the differentiation of glucose, may be measured. Thus, the large magnitude and specificity of the glucose absorption peaks allows the differentiation of glucose from other interfering substances.

Because the human body is comprised mostly of water, it is necessary to differentiate the smaller amount of glucose present in the larger concentration of water in the human body. Water absorbs far- and mid-wavelength infrared energy at most wavelengths. However, an infrared transmission "window" exists in water, in which infrared energy is not completely absorbed. This "window" allows analysis of the 9.3 and 9.6 micron glucose absorption bands because this region of substantially reduced water absorption is the same region in which glucose strongly absorbs. Also, more specifically, in the wavelength range of about 10–11 microns, neither water nor biological substances absorb strongly. Therefore, this wavelength range may also provide reference wavelengths for both water and glucose, allowing their quantification.

On the other hand, the wavelength ranges where water strongly absorbs can be used to determine the absorbance of the target tissue and, therefore, the surface radiation. For example, wavelengths in the range of about 5.9–6.2 microns, may be used to quantify water. Additionally, in the range of about 11.5–13 microns, strong and distinct water absorption peaks exist, providing ideal wavelengths for analyzing the tissue surface temperature.

Other wavelength ranges can be examined. They enhance the ability of the device to differentiate non-water, non-glucose effects in the tissue. For example, radiation has maximum tissue penetration in the 5.0–5.5 wavelength range. Therefore, information about the maximum analytical tissue depth can be obtained in this range where neither $H_2O$ nor biological constituents absorb. Some proteins and some glycosylated proteins are examples of a significant class of interfering substances which interfere with the accurate measurement of glucose in blood. Because proteins have major absorption peaks about the (6.2–6.6), (7.9–8.1), and (9–10) micron wavelength ranges, they can be isolated and compensated for. In addition, an appropriate reference signal for protein can be measured outside of these ranges, for example, at about 8.2 or 8.3 microns.

Different filter combinations can be optimized to detect other interfering analytes as well. In addition to proteins, other materials may be compensated for. Examples of other interfering substances include, but are not limited to, Vitamin C, acetaminophen, alcohol, and urea.

One preferred embodiment, optimized to detect the presence of a glucose analyte in a tissue sample, uses eight filters 720F having the following bandpass center wavelengths: 6.1 $\mu$, 6.9 $\mu$, 8.5 $\mu$, 9.3 $\mu$, 9.7 $\mu$, 10.4 $\mu$, 11.0 $\mu$, and 12.5 $\mu$. Filter combinations using a greater or a fewer number or different filters may be used. Satisfactory filters may be obtained from Optical Coating Laboratory, Inc. (OCLI) of Santa Rosa, Calif. It is contemplated that in accordance with the principles of the present invention, other filters or filter combinations optimized to detect other analytes may be used. Also, other detection methods or devices are contemplated by the present invention. The filtered radiation can be detected by a plurality of detectors 720D, for example, an array of Photo Voltiac Mercury Cadmium Tellerium (PVMCT) detectors. Satisfactory detectors may be obtained from FERMIONICS of Simi Valley, Calif., for example, PV-9.1 detectors with PVA-481-1 preamplifiers may be used. Additionally, room temperature micro-bolometers can be used. These detectors produce an electronic signal which is passed on to a signal processing system 800. Custom circuit boards produced by Optiscan may be used to control temperatures of the detector and the infrared transmissive window assembly. Similar units available from other manufacturers may also be used.

A satisfactory signal processing system 800 is a general purpose programmable personal computer commonly available from companies such as an IBM, Dell, Gateway, etc. Numerous other computers or data processing devices may be used with equal facility. Furthermore, a specialized computer, implemented as hardware, firmware, software or a combination thereof could be devised to accomplish the needed signal processing functions. The computer provides a computational engine, display and user interface. An analog-to-digital (A/D) system may be used to convert analog detector signals to appropriate computer input signals. For example, an acceptable A/D converter is a "PCI-MIO-16XE10" manufactured by National Instruments of Austin, Tex.

It will be appreciated that many modifications can be made to the embodiments described above without departing from the spirit and the scope of the invention.

In particular, it should be noted that many different phase change materials may be used in conjunction with the heat sink as can many different layered window assemblies. Also, if bandpass filters are used in conjunction with the infrared detector, many different filters may be used and said filters may be optimized to detect analytes other than glucose.

The present invention has been particularly shown and described with respect to certain preferred embodiments and the features thereof. It is to be understood that the shown embodiments are the presently preferred embodiments of the present invention and, as such, are representative of the subject matter broadly contemplated by the present invention. The scope of the invention fully encompasses other embodiments which may become obvious to those skilled in the art, and are accordingly to be limited by nothing other than the appended claims, in which reference to an element in the singular is not intended to mean "one and only one" unless explicitly stated, but rather "one or more". All structural and functional equivalents of the elements of the above-described preferred embodiments that are known or later come to be known to those of ordinary skill in the art are expressly incorporated herein by reference and are intended to be encompassed by the present claims. Moreover, it is not necessary for a device or method to address each and every problem solved by the present invention, for it to be encompassed by the present claims. Furthermore, no element, component, or method step in the present disclosure is intended to be depicted to the public regardless of whether the element, component, or method step is explicitly recited in the claims. No claim element herein is to be construed under the provisions of 35 U.S.C. §112, paragraph 6, unless the element is expressly recited using the phrase "means for".

What is claimed is:

1. A device for determining analyte concentrations within sample tissues, the device comprising:

an infrared radiation detector assembly;

an infrared transmissive window in operative combination with the infrared radiation detector assembly;

a cooling element means for inducing a temperature gradient in the sample tissues, the cooling element means being in operative combination with the window and a heating element; and a thermal insulating element in operative combination with said cooling element means and the heating element.

2. A device as in claim 1 wherein said heating element, said cooling element means, and said thermal insulating element are each infrared transmissive elements.

3. A device as in claim 2 wherein said infrared transmissive window is a layered window and said cooling element means and said thermal insulating element each comprise a layer of said layered window.

4. A device as in claim 2–3 wherein said thermal insulating element comprises a layer of said layered window.

5. A device as in claim 4 wherein said heating element is selected from a group consisting of a heat exchanger, an optical heater, an infrared heater, a radio-frequency heater, an electrical resistance heating grid, a thermoelectric heater, and a wire bridge heating grid.

6. A device as in claim 4 wherein said cooling element means is selected from a group consisting of a convection air cooler, a passive conduction cooler, and an active conduction cooler.

7. A device as in claim 1 wherein said heating element is selected from a group consisting of a heat exchanger, an optical heater, an infrared heater, a radio-frequency heater, an electrical resistance heating grid, a thermoelectric heater, and a wire bridge heating grid.

8. A device as in claim 1 wherein said cooling element means is selected from a group consisting of a convection air cooler, a passive conduction cooler, and an active conduction cooler.

9. A device for determining analyte concentrations within sample tissues, the device comprising in operative combination:

a layered window assembly having a plurality of infrared transmissive element means for inducing a temperature gradient in said sample tissue, said infrared transmissive element means including a heating element, a cooling element, and a thermal insulating element;

the thermal insulating element in operative combination with said heating element and said cooling element; and an infrared radiation detector assembly.

10. A device as in claim 9 wherein said heating element comprises a heating grid.

11. A device as in claim 9 wherein said cooling element is a thermal electric cooler.

12. A device as in claim 9 wherein said cooling element further includes a heat sink.

13. A device as in claim 12 wherein said heat sink further includes a phase change material.

14. A device as in claim 9 wherein said infrared radiation detector assembly includes an optical scrambler.

15. The device of claim 9, wherein said device further includes a signal processing system for receiving and processing data from said infrared radiation detector assembly.

16. A device as in claim 9 wherein said infrared radiation detector assembly includes a radiation detector selected from the group consisting of discrete infrared band-pass filters and detectors, an interferometer, a spectrophotometer, a grating monochromator, Fabry-Perot filters, room temperature micro-bolometers, and a variable filter monochromator.

17. A device as in claim 9 wherein said radiation detector comprises a plurality of infrared band-pass filters and detectors optimized for the detection of at least one specific analyte.

18. A device as in claim 17 wherein said infrared radiation detector is optimized for the detection of glucose.

19. A device as in claim 18 wherein said plurality of infrared bandpass filters include filters having bandpass wavelengths of about 9.3 μm and 9.6 μm.

20. A device as in claim 18 wherein said plurality of infrared bandpass filters include filters having bandpass wavelengths in the range of about 8 μm to 9 μm and 10 μm to 11 μm.

21. A device as in claim 17 wherein said plurality of infrared bandpass filters include filters optimized for the measurement of water, said filters having bandpass wavelengths in the range of about 5.9 μm to 6.2 μm and about 11.5 μm to 13 μm.

22. A device as in claim 17 wherein said plurality of infrared bandpass filters include filters optimized for the measurement of water, said filters having bandpass wavelengths in the range of about 10 μm to 11 μm.

23. A device as in claim 17 wherein said plurality of infrared bandpass filters include filters optimized for the measurement of proteins, said filters having bandpass wavelengths in the range of about 6.2 μm to 6.6 μm, 7.9 μm to 8.1 μm, 9.1 μm to 9.4 μm, and 9.4 μm to 9.8 μm.

24. A device as in claim 17 wherein said plurality of infrared bandpass filters include filters optimized for the measurement of proteins, said filters having bandpass wavelengths in the range of about 8.2 μm to 8.3 μm.

25. A device as in claim 17 wherein said plurality of infrared bandpass filters include filters optimized for the measurement of maximum tissue depth information, said filters having bandpass wavelengths in the range of about 5.0 μm to 5.5μm.

26. A device as in claim 17 wherein said plurality of infrared bandpass filters include filters centered at wavelengths of about 6.1 μm, 6.9 μm, 8.5 μm, 9.3 μm, 9.7 μm, 10.4 μm, 11.0 μm, and 12.5 μm.

27. A device as in claim 9 wherein said heating element, and cooling element, induce one of a time varying temperature gradient or a periodically time varying temperature gradient.

28. A device for determining analyte concentrations within sample tissue by measuring sample infrared spectral emissions, the device comprising:

an infrared transmissive window assembly;

a heating element means and a cooling element means each being positioned for heating and cooling the sample tissue, respectively, wherein the heating element means is part of the infrared transmissive window assembly;

an infrared radiation detector assembly positioned such that the infrared spectral emissions from the sample tissue pass through the infrared transmissive window assembly onto a detector; and an infrared transmissive thermally insulating element positioned between said heating element means and said cooling element means.

29. A device for determining analyte concentrations within sample tissue by measuring sample infrared spectral emissions, the device comprising:

an infrared transmissive window assembly;

a heating element means and a cooling element means each being positioned for heating and cooling the sample tissue, respectively, wherein said cooling element means further comprises a heat sink; and an infrared radiation detector assembly positioned such that the infrared spectral emissions from the sample tissue pass through the infrared transmissive window assembly onto a detector.

30. A device for determining analyte concentrations within sample tissue by measuring sample infrared spectral emissions, the device comprising:

an infrared transmissive window assembly;

a heating element means and a cooling element means each being positioned for heating and cooling the sample tissue, respectively; and an infrared radiation detector assembly that is (a) positioned such that the infrared spectral emissions from the sample tissue pass through the infrared transmissive window assembly onto a detector and (b) optimized to detect only selected infrared spectral emissions from said sample tissue.

31. A device as in claim 30 wherein said selected infrared spectral emissions are optimized to detect the presence of glucose in said sample tissue.

32. A device for determining analyte concentrations within sample tissue by measuring sample infrared spectral emissions, the device comprising:

an infrared transmissive window assembly;

a heating element means and a cooling element means each (a) being positioned for heating and cooling the sample tissue, respectively, and (b) configured to induce one of a time varying temperature gradient or a periodically time varying temperature gradient; and an infrared radiation detector assembly positioned such that the infrared spectral emissions from the sample tissue pass through the infrared transmissive window assembly onto a detector.

33. A device for determining analyte concentrations within sample tissues by measuring sample infrared spectral emissions, the device comprising:

an infrared transmissive window assembly;

a means for heating and cooling the sample tissues, wherein the heating and cooling means:

is positioned to heat and cool the sample tissue, is part of the infrared transmissive window assembly, and comprises a heat sink; and an infrared radiation detector assembly positioned such that the infrared spectral emissions from the sample tissue pass through the infrared transmissive window assembly onto a detector.

34. A device as in claim 33 wherein said heating and cooling means further comprises an infrared transmissive thermal insulator.

35. A device for determining analyte concentrations within sample tissues by measuring sample infrared spectral emissions, the device comprising:

an infrared transmissive window assembly;

a means for heating and cooling the sample tissues, the heating and cooling means being positioned to heat and cool the same tissue; and an infrared radiation detector assembly that is (a) positioned such that the infrared spectral emissions from the sample tissue pass through the infrared transmissive window assembly onto a detector and (b) optimized for the detection of glucose in said sample tissue.

36. A device for determining analyte concentrations within sample tissues by measuring sample infrared spectral emissions, the device comprising:

an infrared transmissive window assembly;

a means for heating and cooling the sample tissues, the heating and cooling means being positioned to heat and cool the sample tissue such that the heating and cooling means induces one of a time varying temperature gradient or a periodically time varying temperature gradient; and an infrared radiation detector assembly positioned such that the infrared spectral emissions from the sample tissue pass through the infrared transmissive window assembly onto a detector.

37. A device for determining analyte concentrations within sample tissues, the device generating a thermal gradient in the tissue and measuring infrared spectra to make determinations of analyte concentration, the device comprising in operative combination:

a layered window assembly having a plurality of infrared transmissive elements;

a means for inducing a temperature gradient in the sample tissue, wherein the gradient inducing means:

is in operative combination with the window assembly, is in thermal communication with the sample tissue, and induces one of a time varying temperature gradient or a periodically time varying temperature gradient; and an infrared radiation detector assembly in operative combination with the window.

38. A device for determining analyte concentrations within sample tissues, the device generating a thermal gradient in the tissue and measuring infrared spectra to make determinations of analyte concentration, the device comprising in operative combination:

a layered window assembly having a plurality of infrared transmissive elements;

a means for inducing a temperature gradient in the sample tissue, wherein the gradient inducing means:

is in operative combination with the window assembly, is in thermal communication with the sample tissue, includes an infrared transmissive heating element and a cooling element, and includes an infrared transmissive thermal insulating element positioned to provide thermal insulation between said heating element and said cooling element; and an infrared radiation detector assembly in operative combination with the window.

39. A device for determining analyte concentrations within sample tissues, the device generating a thermal gradient in the tissue and measuring infrared spectra to make determinations of analyte concentration, the device comprising in operative combination:

a layered window assembly having a plurality of infrared transmissive elements;

a means for inducing a temperature gradient in the sample tissue, wherein the gradient inducing means:

is in operative combination with the window assembly, is in thermal communication with the sample tissue, and includes an infrared transmissive heating element and a cooling element that includes a heat sink; and an infrared radiation detector assembly in operative combination with the window.

40. A device as in claim 39 wherein said heat sink further includes a phase change material.

41. A device for determining analyte concentrations within sample tissues, the device generating a thermal gradient in the tissue and measuring infrared spectra to make determinations of analyte concentration, the device comprising in operative combination:

a layered window assembly having a plurality of infrared transmissive elements;

a means for inducing a temperature gradient in the sample tissue, wherein the gradient inducing means:

is in operative combination with the window assembly, is in thermal communication with the sample tissue, and includes an infrared transmissive heating element and a cooling element; and an infrared radiation detector assembly in operative combination with the window, wherein the plurality of infrared transmissive elements include a thermally conductive spreader layer that is positioned between the sample tissue and the heating element and that is formed of a float zone silicon material.

42. A device for determining analyte concentrations within sample tissues, the device generating a thermal gradient in the tissue and measuring infrared spectra to make determinations of analyte concentration, the device comprising in operative combination:

a layered window assembly having a plurality of infrared transmissive elements;

a means for inducing a temperature gradient in the sample tissue, wherein the gradient inducing means:

is in operative combination with the window assembly, is in thermal communication with the sample tissue, and includes an infrared transmissive heating element and a cooling element; and an infrared radiation detector assembly in operative combination with the window, wherein the plurality of infrared transmissive elements include a thermally conductive spreader layer that is positioned between the sample tissue and the heating element and that is formed of a chemical vapor deposited diamond material.

43. A device for determining analyte concentrations within sample tissues, the device generating a thermal gradient in the tissue and measuring infrared spectra to make determinations of analyte concentration, the device comprising in operative combination:

a layered window assembly having a plurality of infrared transmissive elements;

a means for inducing a temperature gradient in the sample tissue, wherein the gradient inducing means:

is in operative combination with the window assembly, is in thermal communication with the sample tissue, and includes an infrared transmissive heating element and a cooling element; and an infrared radiation detector assembly in operative combination with the window, wherein the plurality of infrared transmissive elements include a thermally conductive spreader layer that is positioned between the sample tissue and the heating element and that includes a top side having a protective layer formed thereon.

44. A device as in claim 43 wherein the protective layer is formed of a material which enhances the transmission of infrared energy through said layered window.

45. A device as in claim 43 wherein the protective layer is formed of a mechanically durable wear resistant material.

46. A device as in claim 43 wherein said protective layer is formed of a diamond-like carbon material.

47. A device as in claim 43 wherein said plurality of infrared transmissive elements comprising said layered window assembly include a thermally conductive base layer positioned adjacent to said cooling element.

48. A device as in claim 47 wherein said base layer is formed of a float zone silicon material.

49. A device as in claim 47 wherein said base layer further includes a bottom side having an overcoat layer formed of a broad band anti-reflective material.

50. A device for determining analyte concentrations within sample tissues, the device generating a thermal gradient in the tissue and measuring infrared spectra to make determinations of analyte concentration, the device comprising in operative combination:

a layered window assembly having a plurality of infrared transmissive elements:

a means for inducing a temperature gradient in the sample tissue, the gradient inducing means in operation combination with the window assembly and in thermal communication with the sample tissue; and an infrared radiation detector assembly in operative combination with the window, wherein said infrared radiation detector assembly includes a plurality of discrete infrared bandpass filters and detectors.

51. A device as in claim 50 wherein said plurality of discrete infrared bandpass filters are chosen having bandpass wavelengths optimized to detect a specific analyte.

52. A device as in claim 50 wherein said plurality of discrete infrared bandpass filters include filters having bandpass wavelengths of about 6.1 $\mu$m, 6.9 $\mu$m, 8.5 $\mu$m, 9.3 $\mu$m, 9.7 $\mu$m, 10.4 $\mu$m, 11.0 $\mu$m, and 12.5 $\mu$m.

53. A device for determining analyte concentrations within sample tissues, the device generating a thermal gradient in the tissue and measuring infrared spectra to make determinations of analyte concentration, the device comprising in operative combination:

a layered window assembly having a plurality of infrared transmissive elements;

a means for inducing a temperature gradient in the sample tissue, the gradient inducing means in operation combination with the window assembly and in thermal communication with the sample tissue; and an infrared radiation detector assembly in operative combination with the window, wherein said infrared radiation detector assembly further comprises a high reflectance scrambler.

54. An infrared transmissive patient window comprising in operative combination:

a plurality of layered infrared transmissive element means for inducing a temperature gradient in a sample tissue, including a heating element and a thermal insulating element.

55. The window of claim 54, in which said plurality of layered infrared transmissive element means further includes a spreader layer and a base window.

56. The window of claim 55, wherein said spreader layer is positioned adjacent to said heating element, the heating element being adjacent to said thermal insulating element, and said thermal insulating element being positioned adjacent to said base window.

57. The window of claim 56, wherein said spreader layer includes a top surface having a protective layer, said protective layer being formed of an infrared transmissive material which enhances the energy transmission of said window and having high thermal conductivity and having a high mechanical wear resistance.

58. The window of claim 57, wherein said base window includes a bottom surface having an overcoat layer.

59. The window of claim 54, wherein said heating element and thermal insulating element induces one of a time varying temperature gradient or a periodically time vary temperature gradient.

60. A method for making a device for generating a thermal gradient in a sample tissue and measuring infrared spectra to determine analyte concentrations in the sample, the method comprising the steps of:

providing a layered window assembly having a plurality of infrared transmissive elements, wherein the plurality of infrared transmissive elements includes an infrared transmissive thermal insulating element;

providing a means for inducing a temperature gradient, the gradient inducing means in operative combination with the window;

providing an infrared radiation detector in operative combination with the window; and providing a signal processing system in operative combination with the radiation detector.

61. The method of claim 60 wherein said step of providing a means for inducing a temperature gradient further includes the step of providing a heating element and a cooling element with said infrared transmissive thermal insulating element disposed therebetween.

62. The method of claim 61 wherein said step of providing a layered window assembly having a plurality of infrared transmissive element means includes providing said heating element as one of said plurality of infrared transmissive elements.

63. The method of claim 62 wherein said step of providing a layered window assembly having a plurality of infrared transmissive element means includes providing a first thermally conducting infrared transmissive element, said first thermally conducting element having a top surface and a bottom surface, said top surface having an infrared transmissive protective layer being disposed thereon, said protective layer being disposed adjacent to said sample tissue.

64. The method of claim 63 wherein said step of providing said heating element as one of said plurality of infrared transmissive element means includes positioning said heating element adjacent to said bottom surface of said first thermally conducting element.

65. The method of claim 61 wherein said step of providing said heating element includes the further step of selecting said heating element from the group consisting of a heat exchanger, an optical heater, an infrared heater, a radio-frequency heater, an electrical resistance heating grid, a thermoelectric heater, and a wire bridge heating grid.

66. The method of claim 61 wherein said step of providing an infrared radiation detector in operative combination with said window includes the further step of selecting said infrared radiation detector from the group consisting of discrete infrared bandpass filters and detectors, an interferometer, a spectrophotometer, a grating monochromator, tunable Fabry-Perot filters, and a variable filter monochromator.

67. The method of claim 66 wherein said step of providing an infrared radiation detector includes the step of providing a plurality of discrete infrared bandpass filters which are interchangeable.

68. The method of claim 67 wherein said step of providing said plurality of discrete infrared bandpass filters includes providing filters having bandpass wavelengths of about 6.1 μm, 6.9 μm, 8.5 μm, 9.3 μm, 9.7 μm, 10.4 μm, 11.0 μm, and 12.5 μm.

* * * * *